US008858436B2

(12) United States Patent  
Pagoulatos et al.

(10) Patent No.: US 8,858,436 B2  
(45) Date of Patent: Oct. 14, 2014

(54) SYSTEMS AND METHODS TO IDENTIFY INTERVENTIONAL INSTRUMENTS

(75) Inventors: Nikolaos Pagoulatos, Bothell, WA (US); Qinglin Ma, Woodinville, WA (US)

(73) Assignee: SonoSite, Inc., Bothell, WA (US)

( * ) Notice: Subject to any disclaimer, the term of this patent is extended or adjusted under 35 U.S.C. 154(b) by 1023 days.

(21) Appl. No.: 12/269,663

(22) Filed: Nov. 12, 2008

(65) Prior Publication Data

US 2010/0121190 A1    May 13, 2010

(51) Int. Cl.
*A61B 8/00* (2006.01)
*A61B 8/08* (2006.01)
*G06T 7/20* (2006.01)

(52) U.S. Cl.
CPC . *A61B 8/00* (2013.01); *A61B 8/483* (2013.01); *G06T 7/2033* (2013.01); *A61B 8/461* (2013.01); *G06T 2207/30021* (2013.01)
USPC ........................................................ 600/437

(58) Field of Classification Search
CPC .......... A61B 8/00; A61B 8/461; A61B 8/483; G06T 7/2033; G06T 2207/30021
USPC .................................. 600/424, 437; 382/131
See application file for complete search history.

(56) References Cited

U.S. PATENT DOCUMENTS

| | | | |
|---|---|---|---|
| 5,603,318 A | 2/1997 | Heilbrun et al. | |
| 6,233,476 B1 * | 5/2001 | Strommer et al. | 600/424 |
| 6,317,621 B1 * | 11/2001 | Graumann et al. | 600/424 |
| 6,490,477 B1 * | 12/2002 | Zylka et al. | 600/429 |
| 6,591,130 B2 * | 7/2003 | Shahidi | 600/424 |
| 7,386,339 B2 | 6/2008 | Strommer et al. | |
| 2002/0165448 A1 * | 11/2002 | Ben-Haim et al. | 600/424 |
| 2003/0050557 A1 * | 3/2003 | Susil et al. | 600/424 |
| 2003/0130576 A1 | 7/2003 | Seeley et al. | |
| 2003/0135119 A1 | 7/2003 | Lee et al. | |
| 2007/0073136 A1 | 3/2007 | Metzger | |
| 2007/0100234 A1 | 5/2007 | Arenson et al. | |
| 2007/0193354 A1 | 8/2007 | Felix et al. | |
| 2008/0119735 A1 | 5/2008 | Lin et al. | |
| 2008/0221425 A1 | 9/2008 | Olson et al. | |
| 2008/0269610 A1 | 10/2008 | Burla et al. | |

OTHER PUBLICATIONS

Cox, AFNI: Software for Analysis and Visualization of Functional Magnetic Resonance Neuroimages, Computers and Biomedical Research 29, 162-173, 1996.*
International Search Report and the Written Opinion issued for PCT/US2009/062976, dated Jan. 7, 2010, 11 pages.

* cited by examiner

*Primary Examiner* — Long V. Le
*Assistant Examiner* — Bo J Peng
(74) *Attorney, Agent, or Firm* — Perkins Coie LLP

(57) ABSTRACT

Systems and methods which operate to identify interventional instruments and/or other objects in images are shown. Embodiments operate to extract relevant information regarding interventional instruments from a multi-dimensional volume for presenting the information to a user in near real-time with little or no user interaction. Objects may be identified by segmenting a multi-dimensional volume, identifying a putative object of interest in multiple multi-dimensional volume segments, and determining a position of the object of interest within the multi-dimensional volume using the putative object of interest segment identifications. Identification of objects of interest according to embodiments may be utilized to determine an image plane for use in displaying the objects within a generated image, to track the objects within the multi-dimensional volume, etc., such as for medical examination, interventional procedures, diagnosis treatment, and/or the like.

15 Claims, 6 Drawing Sheets

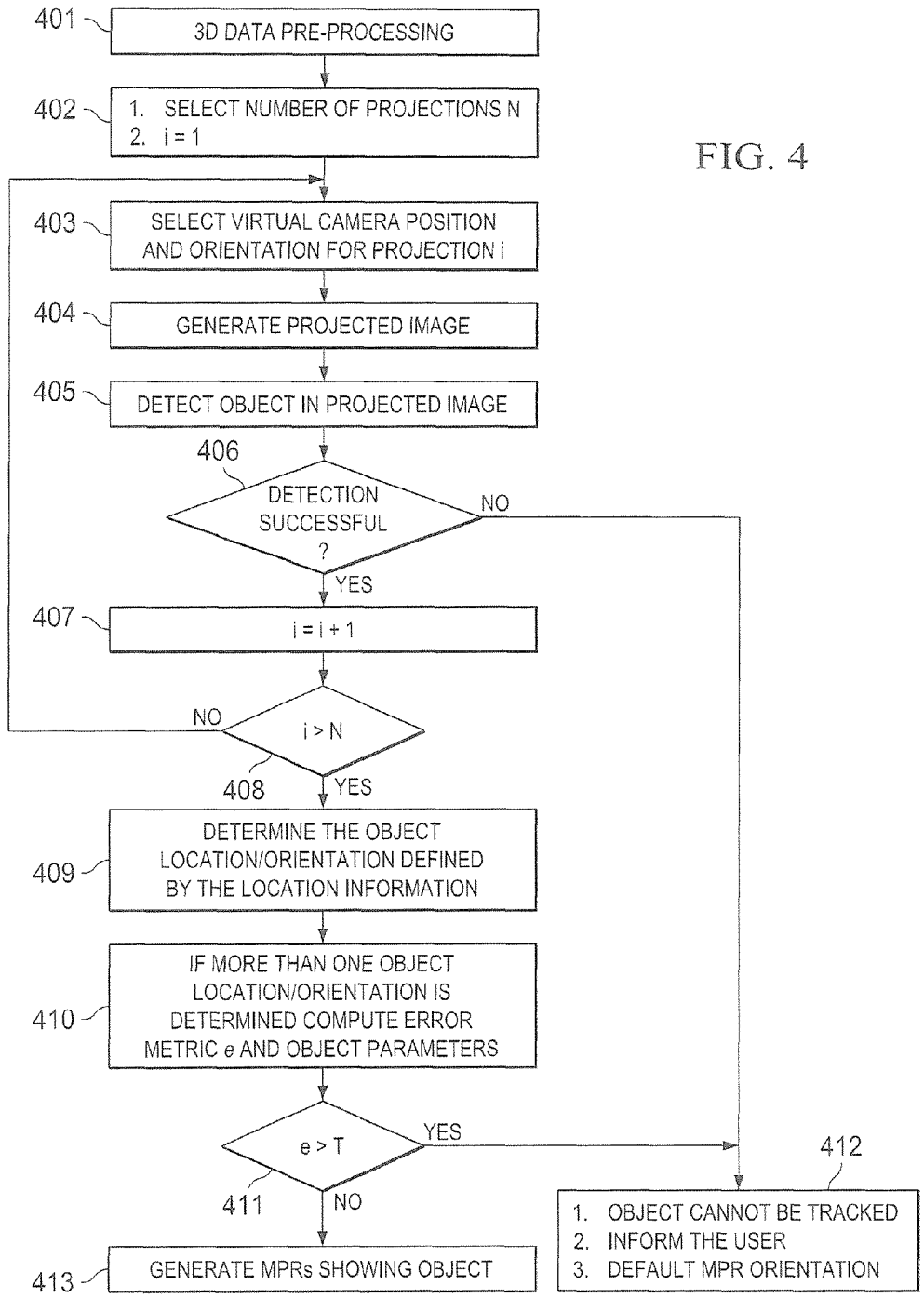

SYSTEMS AND METHODS TO IDENTIFY INTERVENTIONAL INSTRUMENTS

REFERENCE TO RELATED APPLICATIONS

The present application is related to co-pending and commonly assigned U.S. patent application Ser. No. 12/269,623, entitled "Systems and Methods for Image Presentation for Medical Examination and Interventional Procedures", filed Nov. 12, 2008, the disclosure of which is hereby incorporated herein by reference.

TECHNICAL FIELD

The invention relates generally to identifying interventional instruments and, more particularly, to segmenting and/or tracking interventional instruments in a multi-dimensional volume, such as for medical examination, interventional procedures, diagnosis, treatment, etc.

BACKGROUND OF THE INVENTION

Various forms of imaging apparatus have been used extensively for medical applications. For example, fluoroscope systems, X-ray imaging systems, ultrasound imaging systems, computed tomography (CT) imaging systems, and magnetic resonance (MR) imaging (MRI) systems have been used for a number of years. Any number of medical examination, interventional procedures, diagnosis, and/or treatment may be provided using an appropriate one of the foregoing systems suited for the task.

Ultrasound imaging systems have been used as a tool for assisting interventional clinical procedures. For example, conventional two-dimensional (2 D) ultrasound imaging has been used in the field of regional anesthesia to provide a way of "seeing" and tracking the delivery of the anesthetic with a needle, rather than attempting to achieve such a goal blindly using nerve stimulation technology. However, such 2D imaging brings with it many issues associated with training and ease-of-use. Anesthesiologists who are new to ultrasound imaging often relatively rapidly acquire the skill required for interpreting the location and orientation of the 2D plane presented in a conventional 2D image. However, it is significantly more difficult for the anesthesiologist to master the hand-eye coordination required to obtain both the target anatomy (e.g., nerve) and the interventional apparatus (e.g., needle) in the same 2D image, while trying to guide the interventional apparatus towards the target. Even more problematic, it is often difficult for the anesthesiologist to control the 2D image such that the interventional apparatus is meaningfully presented or shown in the 2D image.

A major reason for the hand-eye coordination problem in image-guided (e.g., ultrasound image-guided) interventional procedures is the fact that a 2D image is essentially a thin slice of a 3D space in which the observer is working within. Coordinating both hands for providing continuous alignment between a 3D object in space (e.g., a needle) and a relatively thin 2D slice (the image plane), while maintaining the anatomy of interest (e.g., nerve) within the image plane by observing the image displayed in the imaging device is understandably a very difficult task. These problems are not limited to the foregoing anesthesiologist example, but are present with respect to many interventional procedures, such as biopsies, line placements, catheter placements, etc.

Computing technology, having progressed dramatically in the last few decades, has provided three-dimensional (3D) (e.g., a data set providing information in an X, Y, and Z axes space) and even four-dimensional (4D) (e.g., a 3D image having a time axis added thereto) imaging capabilities. Although such 3D and 4D imaging technology arose from disciplines such as drafting, modeling, and even gaming, the technology has been adopted in the medical field. For example, computed tomography has been utilized with respect to X-ray images to produce 3D images. Furthermore, computerized 3D rendering algorithms have been utilized to enhance the visualization of 3D datasets from various imaging modalities including CT, MR, ultrasound etc.

The use of such computing technology to provide 3D and 4D images in the medical field has carried with it several disadvantages from its origins. For example, providing biaxial freedom of movement/rotation with respect to each of the X, Y, and Z axes (i.e., 6 degrees of freedom), as derived from the drafting and modeling roots of 3D imaging, has typically been provided with respect to medical imaging where 3D and 4D imaging is available. Such degrees of freedom can be used to allow 2D cross-section images through a 3D volume (e.g., multi-planar reconstruction (MPR) images) in any plane. Particular orientations, such as top, bottom, left, and right, are often less important in the virtual world than presenting a desired portion of the rendered image to a viewer. Accordingly, object image (e.g., volume rendered image) and cross-section image (e.g., MPR image) orientation freedom has been provided by 3D and 4D image computing technology. However, providing such freedom with respect to certain medical imaging tasks has further compounded the aforementioned hand-eye coordination problems with respect to interventional procedures. Moreover, users in the medical field, such as the aforementioned anesthesiologists who are new to ultrasound imaging, often find it difficult if not impossible to control such images to locate and/or present the interventional apparatus and/or target in a meaningful way.

Several attempts have been made to facilitate identification of interventional instruments in images and/or framing interventional instruments within images. For example, sensor configurations, such as magnetic sensors, light sensors, etc., have been implemented with respect to various interventional instruments and corresponding imaging tools in order to facilitate identification of interventional instruments in images. Additionally, apparatus, such as needle guides, have been added for use with respect to interventional instruments and imaging tools in order to place the interventional instrument within the generated images. Likewise, complex systems, such as gyroscopes, have been implemented with respect to imaging tools and/or interventional instruments in order to facilitate placing interventional instruments within images. The foregoing attempts, however, require structural modification to the interventional instruments and/or imaging tools. Such modifications are often quite complex and expensive, and in all cases limits the particular interventional instruments and/or imaging tools which are available to a user seeking to receive the benefit of such techniques.

BRIEF SUMMARY OF THE INVENTION

The present invention is directed to systems and methods which operate to identify interventional instruments and/or other objects in images. For example, embodiments of the invention operate to extract relevant information regarding interventional instruments from a multi-dimensional volume (e.g., a 3D ultrasound field-of-view (FOV)) for presenting the information to a user in near real-time (e.g., perceived by the user as occurring in real-time) with little or no user interaction. In operation, embodiments assist image-guided interventional procedures by providing means to facilitate rapid visualization of interventional instruments and anatomical targets using volumetric data sets.

Embodiments operate to select an image plane for displaying an interventional instrument and, in near real-time, updating a generated image and the image plane to track the interventional instrument during a procedure. For example, once an interventional instrument is identified in a multi-dimensional volume, image planes may be selected from within the multi-dimensional volume to show the interventional instrument, such as to provide a broadside view of the interventional instrument. As the interventional instrument is manipulated during a procedure, embodiments of the invention may operate to adjust the image plane accordingly so as to track the interventional instrument throughout the procedure. Accordingly, embodiments of the invention operate not only to select image planes for displaying images of an interventional instrument, but also operate to adjust the display to continuously show the interventional instrument.

Objects are preferably identified by segmenting a multi-dimensional volume, identifying a putative object of interest (e.g., interventional instrument) in multiple multi-dimensional volume segments, and calculating or otherwise determining a position of the object of interest within the multi-dimensional volume using the putative object of interest segment identifications. Accordingly, a three-dimensional problem of identification of an object in space is broken down into multiple two-dimensional problems, according to embodiments of the invention. Identification of objects of interest according to embodiments of the invention may be utilized to identify and display the objects within a generated image, to track the objects within the multi-dimensional volume, etc., such as for medical examination, interventional procedures, diagnosis, treatment, and/or the like. Accordingly, operation according to embodiments adaptively extracts the relevant cross-sections of a multi-dimensional volume which show one or more objects of interest, such as interventional instruments, target anatomy, etc., for presentation to a user.

The foregoing identification of interventional instruments and/or other objects may be performed automatically, semi-automatically, and/or manually according to embodiments of the invention. For example, embodiments of the present invention may operate to semi-automatically identify interventional instruments by enabling a user to select objects within segments of a multi-dimensional volume as putative interventional instrument locations. Thereafter, this information may be utilized to calculate a position of the interventional instrument within the multi-dimensional volume. Additionally or alternatively, embodiments of the invention may operate to automatically (e.g., without user input) identify objects within segments of a multi-dimensional volume as putative interventional instrument locations, such as using fuzzy logic and/or other machine implemented identification logic. For example, logic algorithms may operate to identify relative brightness, object shape, relative location, segment-to-segment relationships, etc. in order to identify an object as a putative interventional instrument within a particular multi-dimensional volume segment. This information is utilized by embodiments of the present invention to calculate a position of the interventional instrument within the multi-dimensional volume. Calculation of the interventional instrument position may implement segmentation principles as well as geometrical principles to identify the interventional instrument throughout the volume.

Embodiments of the invention implement techniques for verifying that putative interventional instrument locations correspond to the actual location of an interventional instrument. For example, multiple sets of putative interventional instrument locations are cross-checked in order to confirm that each such set identifies a same interventional instrument location, or identifies interventional instrument locations within a threshold level of accuracy, according to embodiments of the invention. Additionally or alternatively, different putative interventional instrument location identification techniques, such as user selected, relative brightness, object shape, tissue motion, etc., may be utilized to cross-check or otherwise confirm accuracy of interventional instrument identification according to embodiments of the invention.

Interventional instruments as may be identified according to embodiments of the invention include such apparatus as needles, catheters, stents, surgical tools, and/or other medical devices. Accordingly, an application for embodiments described herein may include identifying an interventional instrument being used in a surgical or other medical procedure that requires precision positioning and movement of the interventional instrument. Thus, embodiments of the invention may be utilized to identify the interventional instrument in near real-time during the medical procedure to appropriately select an image plane including the interventional instrument to display an image having the interventional instrument to the clinician. Moreover, embodiments of the invention may operate to track the interventional instrument within the multi-dimensional volume so as to provide appropriate and useful updated (e.g., moving) images wherein the interventional instrument remains appropriately displayed.

Having identified an interventional instrument and/or other object within a multi-dimensional volume, embodiments of the invention operate to cause an image for appropriately displaying the object or objects to be generated, wherein the objects' movement within the volume is shown in near real-time. The generated images preferably show both an interventional instrument as well as other points of interest or reference within the multi-dimensional volume. A resulting image may be provided with or in association with one or more reference indicator, such as in the form of a marker or markers, to correlate sides, dimensions, etc. of the image and/or volume dataset from which the image was generated with the physical world.

It should be appreciated that the foregoing embodiments may be utilized in addressing difficulties associated with hand-eye coordination in image-guided interventional procedures. For example, embodiments of the invention reduce the complexity of using 4D imaging by implementing semi-automatic or automatic segmentation and tracking algorithms that process 3D data sets or image volumes in near real-time to present the user with one or more 2D slices that contain the object or objects of interest (e.g., needle, catheter, surgical tool, anatomical target, etc.) as if 2D imaging is used. Although 4D imaging techniques may be employed, a user may be readily presented with an image or images (e.g., 2D and/or 3D image) having one or more objects of interest properly and appropriately therein to provide the user with desired information. This image presentation is preferably maintained in near real-time to track the identified objects throughout the procedure. Accordingly, the workflow of image-guided interventional procedures is greatly improved due to there being a high probability that an object, such as an interventional instrument, will be contained within a 3D volume rather than a thin slice associated with a 2D image plane. Although a clinician may still need to manipulate an imaging tool (e.g., ultrasound transducer) to find a target of interest (e.g. anatomical structure), once such a target has been acquired few or no additional image tool manipulations will be needed while guiding an interventional instrument to the target of interest according to embodiments of the invention. According to embodiments of the invention, the image plane and orientation of a generated image is locked to an identified interventional instrument to thereby reliably and accurately display the interventional instrument regardless of its changing positions in any dimension of the volume.

Because embodiments of the invention operate to provide an image having fewer dimensions (e.g., 2 dimensions) than a multi-dimensional (e.g., three or four dimensional) data set from which the images are generated, such multi-dimensional data sets may additionally be utilized to provide additional information to a user. For example, images in addition to an image appropriately showing an interventional instrument or other object may be provided to the user. Such additional images may be useful in enhancing the user's understanding of the anatomy with respect to the interventional instrument, to increase the user's confidence in performing the procedure, etc. As one example, in the case of ultrasound image-guided nerve blocks, physicians can have a better understanding of drug spread after the injection by simultaneously observing multiple cross-sections of the nerve, as may be generated from a 4D data set.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is low made to the following descriptions taken in conjunction with the accompanying drawing, in which:

FIG. 4 shows a flow diagram of operation to identify one or more objects of interest according to an embodiment of the invention;

DETAILED DESCRIPTION OF THE INVENTION

Figure 1A:
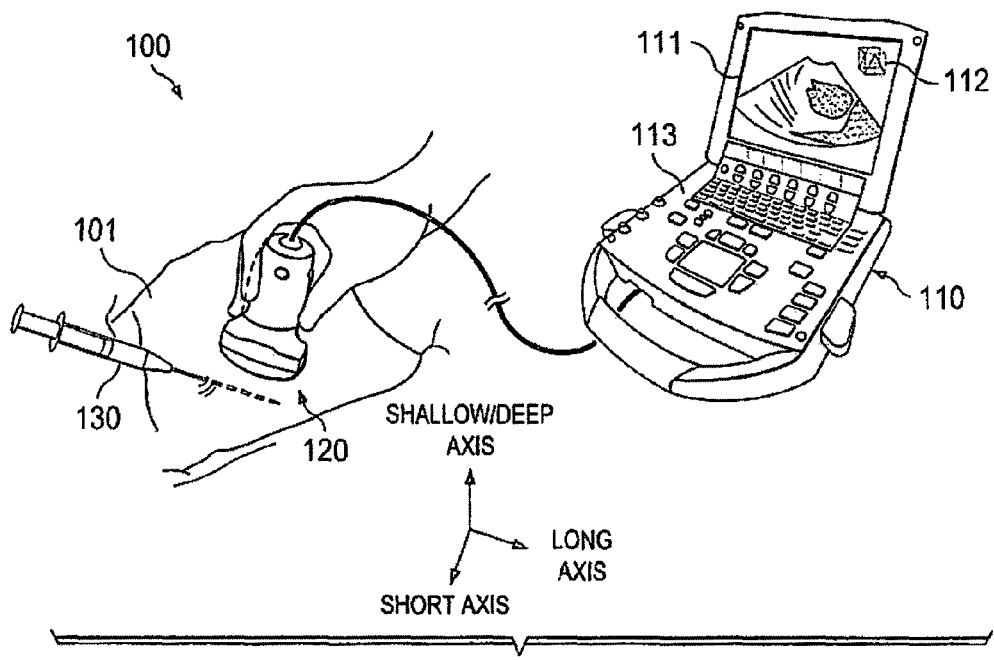
FIG. 1A shows a system adapted according to an embodiment of the present invention.

Directing attention to FIG. 1A, a system adapted according to embodiments of the invention is shown as system 100. System 100 may, for example, comprise a diagnostic ultrasound system operable to provide 2D and/or 3D images from a multi-dimensional (e.g., 3D and/or 4D) volume dataset. Although embodiments of the invention are described herein with reference to ultrasound imaging technology, in order to aid the reader in understanding the invention, it should be appreciated that the concepts of the present invention are not limited in applicability to ultrasound imaging. For example, embodiments of the present invention may be implemented with respect to fluoroscope systems, X-ray imaging systems, ultrasound imaging systems, CT imaging systems, MRI systems, positron emission tomography (PET) imaging systems, and the like.

System 100 of the illustrated embodiment includes system unit 110 and transducer 120 coupled thereto. System unit 110 preferably comprises a processor-based system, such as shown in the high level block diagram of FIG. 1B. Transducer 120 may comprise a transducer configuration corresponding to the imaging technology used.

Figure 1B:
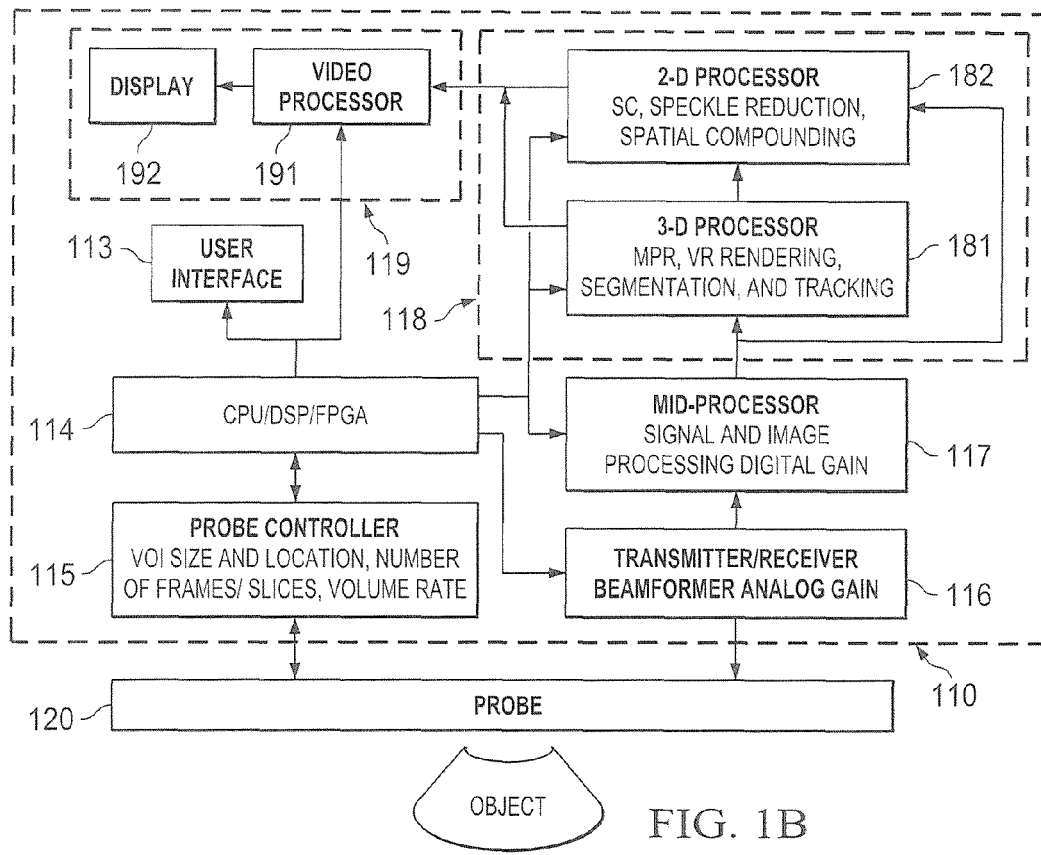
FIG. 1B shows a high level block diagram of an embodiment of the system of FIG. 1A.

System unit 110 illustrated in FIG. 1B includes processor 114, such as may comprise a central processing unit (CPU), digital signal processor (DSP), field programmable gate array (FPGA), and/or the like, preferably having memory associated therewith. In embodiments, the processor-based system of system unit 110 may comprise a system on a chip (SOC), for example. Probe controller 115 of system unit 110 shown in FIG. 1B provides image dataset collection/acquisition control, such as to control the volume of interest size and location, the volume rate, the number of imaging slices used for image acquisition, etc. Front-end circuitry 116 of the illustrated embodiment provides signal transmission to drive probe 120, beamforming for transmission and/or reception of ultrasonic pulses, signal conditioning such as filtering, gain control (e.g., analog gain control), etc. Mid-processor 117 of the illustrated embodiment, operable under control of processor 114, provides signal and image processing, additional signal conditioning such as gain control (e.g., digital gain control), decimation, low-pass filtering, demodulation, re-sampling, lateral filtering compression, amplitude detection, blackhole filling, spike suppression, frequency compounding, spatial compounding, decoding, and/or the like.

According to the illustrated embodiment, signals processed by mid-processor 117 are provided to back-end processor 181 for further image processing. Back-end processor 118 of the illustrated embodiment includes 3D processor 181 and 2D processor 182. 3D processor 181, operating under control of processor 114, produces 3D image volumes and images therefrom (e.g., MPR images, VR images) for presentation by display system 119 as image 111. 3D processor 181 of the illustrated embodiment further provides for image volume segmentation, image plane determination, interventional instrument tracking, gray mapping, tint mapping, contrast adjustment, MPR generation, volume rendering, surface rendering, tissue processing, and/or flow processing as described herein. 2D processor 182, operating under control of processor 114, provides scan control, speckle reduction, spatial compounding, and/or the like.

User interface 113 of embodiments may comprise keyboards, touch pads, touch screens, pointing devices (e.g., mouse, digitizing tablet, etc.), joysticks, trackballs, spinner knobs, buttons, microphones, speakers, display screens (e.g., cathode ray tube (CRT), liquid crystal display (LCD), organic LCD (OLCD), plasma display, back projection, etc.), and/or the like. User interface 113 may be used to provide user control with respect to multi-dimensional image mode selection, image volume scanning, object tracking selection, depth selection, gain selection, image optimization, patient data entry, image access (e.g., storage, review, playback, etc.), and/or the like. Display system 119, comprising a part of user interface 113 of embodiments of the invention, includes video processor 191 and display 192. Video processor 191 of embodiments provides video processing control such as overlay control, gamma correction, etc. Display 192 may, for example, comprise the aforementioned CRT, LCD, OLCD, plasma display, back projection display, etc.

Logic of system unit 110 preferably controls operation of system 100 to provide various imaging functions and operation as described herein. Such logic may be implemented in hardware, such as application specific integrated circuits (ASICs) or FPGAs, and/or in code, such as in software code, firmware code, etc.

According to a preferred embodiment, transducer 120 comprises one or more transducer elements (e.g., an array of ultrasound transducers) and supporting circuitry to illuminate (e.g., insonify) a target, capture data (e.g., ultrasound echos), and provide target data (e.g., transducer response signals) to system unit 110 for use in imaging. Transducer 120 of the embodiment illustrated in FIG. 1B may, for example, comprise any device that provides conversion between some form of energy and acoustic energy, such as a piezoelectric transducer, capacitive micro-machined ultrasonic transducer (CMUT), a piezoelectric micro-machined ultrasonic transducer (PMUT), etc. Where system unit 110 comprises an ultrasound imaging system unit, transducer 120 may comprise any of a number of ultrasound transducer configurations, such as a wobbler configuration, a 1D matrix array configuration, a 1.5D matrix array configuration, a 1.75D matrix array configuration, a 2D matrix array configuration, a linear array, a curved array, etc. Moreover, transducer 120 may be adapted for particular uses, procedures, or functions. For example, transducers utilized according to embodiments of the invention may be adapted for external use (e.g. topological), internal use (e.g., esophageal, vessel, rectal, vaginal, surgical, etc.), cardio analysis, OB/GYN examination, etc.

It should be appreciated that, although the embodiment illustrated in FIG. 1B shows one particular division of functional blocks between system unit 110 and transducer 120, various configurations of the division of functional blocks between the components of system 100 may be utilized according to embodiments of the invention. For example, beamformer 116 may be disposed in transducer 120 according to embodiments of the invention. Moreover, although a particular combination of functional blocks are shown to comprise system unit 110 of the illustrated embodiment, it should be appreciated that functions performed by embodiments of the invention may be provided by one or more system units. For example, traditional image data collection and processing functions may be provided by an imaging system unit, such as a portable ultrasound system, and extended image processing functions according to embodiments of the invention may be provided by one or more system unit (e.g., an external personal computer (PC) system unit) in communication therewith.

In the illustrated embodiment, system 100 is being used with respect to an interventional procedure. Specifically, transducer 120 is being held against object 101, such as may comprise a portion of a human body, to illuminate an area targeted for an interventional procedure. Interventional apparatus 130, such as may comprise a hypodermic needle, a catheter, a portacath, a stent, an intubation tube, endoscope, etc., is being inserted into object 101 in an area illuminated by transducer 120. Accordingly, an image, shown as image 111, is generated by system unit 110 in an effort for a user to visually monitor the progression, placement, and/or use of interventional apparatus 130.

System unit 110 may provide various signal and/or image processing techniques in providing image 111, such as tissue harmonic imaging (THI), demodulation, filtering, decimation, interpretation, amplitude detection, compression, frequency compounding, spatial compounding, black hole fill, speckle reduction, etc. Image 111 may comprise various forms or modes of images, such as color images, B-mode images, M-mode images, Doppler images, still images, cine images, live images, recorded images, etc.

Figure 2A:
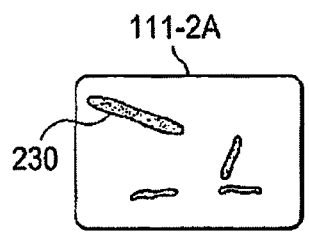
FIGS. 2A and 3A show exemplary images as may be generated by the system of FIG. 1A.
Figure 3A:
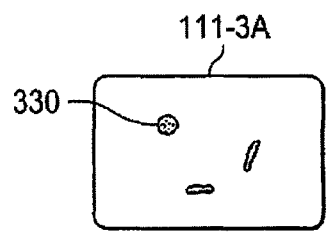
Figure 2B:
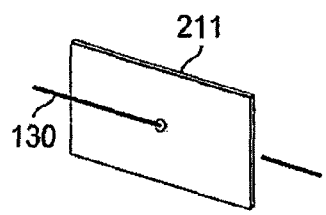
FIGS. 2B and 3B show the image planes of a respective one of the images of FIGS. 2A and 3A.
Figure 3B:
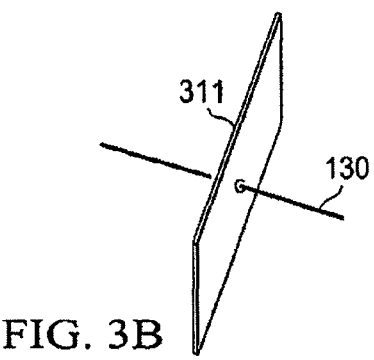

In operation according to traditional imaging techniques, it is often difficult for a user to effectively utilize a system such as system 100 with respect to an interventional apparatus. For example, the generated images often provide a 2D imaging plane which may not readily be oriented to provide the needed information. Directing attention to FIG. 2A, image 111-2A is shown presenting a 2D imaging plane (imaging plane 211 of FIG. 2B) along the long axis of transducer 120 (e.g., an ultrasound transducer array longitudinal axis). Similarly, image 111-3A of FIG. 3A presents a 2D imaging plane (imaging plane 311 of FIG. 3B) along the short axis of transducer 120 (e.g., an ultrasound transducer array latitudinal axis).

The longitudinal axis of interventional apparatus 130 is in a plane oriented at a slightly different angle than that of imaging plane 211. Thus, only a relatively small portion of interventional apparatus 130 is visible in image 111-2A as object 230. The longitudinal axis of intervention apparatus 130 is in a plane oriented at an acute angle with respect to that of imaging plane 311. Thus, even a smaller portion of interventional apparatus 130 is visible in image 111-3A as object 330. These relatively small portions of interventional apparatus 130 may not provide visualization of all relevant or desired portions of interventional apparatus 130, such as a distal end, an operative portion, etc. Accordingly, a user is unlikely to be provided with desired information with respect to an interventional procedure from either image 111-2A or 111-3A. Moreover, it is often difficult, if not impossible, for a user to manipulate a transducer with sufficient precision to generate an image providing desired information with respect to an interventional procedure. For example, experience has shown that it is unproductively difficult to attempt to manipulate an ultrasound transducer, providing a 2D planar view of a target area, sufficiently to capture the length of an interventional apparatus within an image. This is often referred to as hand/eye coordination difficulty.

It should be appreciated that typical 3D or 4D imaging technology may not fully address the need with respect to providing imaging in association with interventional procedures. For example, although transducer 120 may be utilized to generate a multi-dimensional (e.g., 3D or 4D) volume dataset from which a volume rendered image may be generated, display of a 3D or 4D object image may not readily convey the needed or desired information. Although an object of interest may be contained in the volume dataset, it may require considerable manipulation to find an image plane that shows the object in a meaningful way. Moreover, where freedom of movement/rotation with respect to each of the X, Y, and Z axes is allowed, the user may not be able determine the orientation of the objects represented, and thus be unable to identify a target object or other objects of interest.

It is often desirable to view both the anatomy and the interventional instrument. Accordingly, a volume rendered image or surface rendered image alone generally does not provide the best fit. Although MPR images, as may be rendered from a multi-dimensional volume dataset generated using transducer 120, comprise 2D images and thus may be used to present an image format that is more readily interpreted by a user and which are suited for display on a 2D output device, control of system unit 110 to display a desired MPR image often proves unproductively difficult. For example, a user may desire to generate a MPR image for an image plane corresponding to the longitudinal axis of interventional apparatus 130 from a multi-dimensional dataset. However, controlling system unit 110 to identify that image plane, such as through input of pitch, yaw, and roll control, may be quite complicated. Moreover, the degrees of freedom available to the user may result in an inability for the user to identify a best MPR image (e.g., the user may be presented with the ability to generate so many variations of images that the best image may never be arrived at). Once generated, the user may be unable to determine the orientation of the image and/or objects therein (e.g., the target object) and thus may be unable to meaningfully interpret the image.

Embodiments of the present invention operate to identify objects of interest, such as interventional apparatus 130, within a multi-dimensional volume in order to extract relevant information regarding the object for presenting the information to a user in near real-time with little or no user interaction. In operation according to a preferred embodiment, logic of system unit 110 operates to segment a multi-dimensional volume and calculate a position of interventional apparatus 130 within the multi-dimensional volume using information identifying a putative object of interest within multiple segments. Such identification of interventional apparatus 130 may be utilized to select an image plane to appropriately orient and show interventional apparatus 130 for display in image 111. Embodiments preferably operate to lock the image plane used in generating image 111 to interventional apparatus 130 to track the interventional apparatus within the multi-dimensional volume, such as for medical examination, interventional procedures, diagnosis, treatment, and/or the like. For example, logic of system unit 110 may continuously operate to segment the multi-dimensional volume and calculate the position of interventional apparatus 130 within the multi-dimensional volume for near real-time updating the image, such as by continuing to use information identifying the object of interest, tracking or updating previously identified putative locations of the object of interest, using frame-to-frame image comparisons, and/or the like. Accordingly, operation according to embodiments adaptively extracts relevant cross-sections of a multi-dimensional volume to show interventional apparatus 130, perhaps with one or more additional objects of interest, for presentation to a user. Automated interventional instrument tracking may be provided through use of various techniques, such as image based analysis, using one or more sensors, etc.

Directing attention to FIG. 4, a flow diagram of operation of a system (e.g., system 100) to identify one or more objects of interest (e.g., interventional apparatus 130) in a multi-dimensional volume according to embodiments of the invention is shown. Interventional instrument 130 may, for example, be an apparatus such as a needle, catheter, stent, surgical tool, and/or other medical device. Accordingly, operation of the flow diagram set forth in FIG. 4 may operate to identify an interventional instrument being used in a surgical or other medical procedure that requires precision positioning and movement of the interventional instrument. Thus, the illustrated method may be utilized to identify interventional apparatus 130 in near real-time during the medical procedure to appropriately show interventional apparatus 130 within an image presented to the clinician. Moreover, the method may operate to track the interventional instrument within the multi-dimensional volume so as to provide appropriate and useful updated (e.g., moving) images wherein the interventional instrument is and remains appropriately displayed.

Figure 5A:
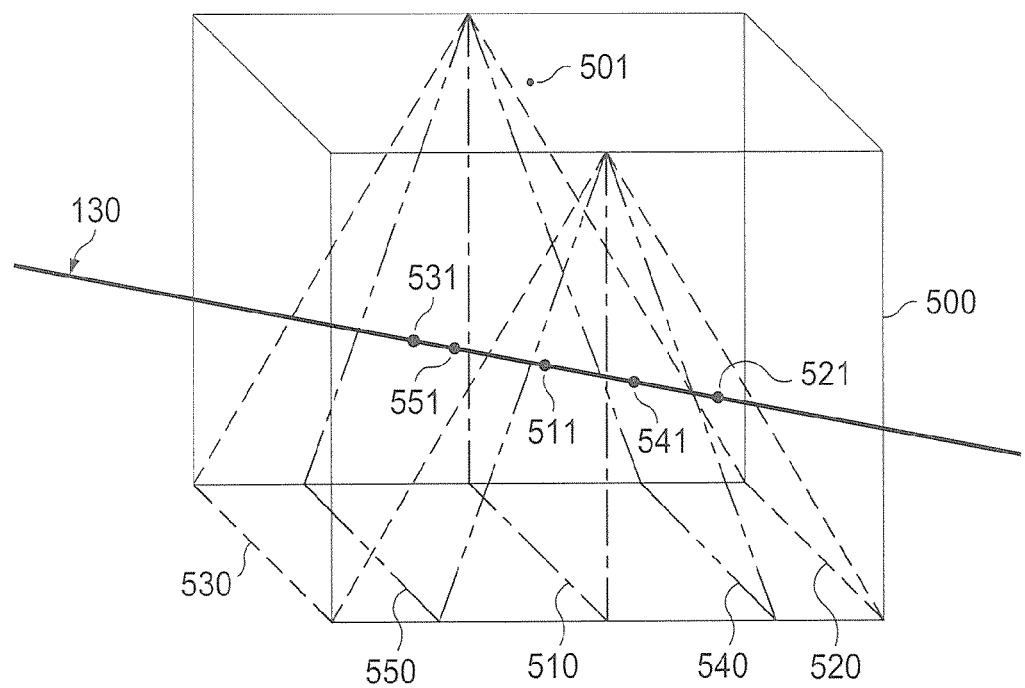
FIGS. 5A-5C show image projections utilized in identifying one or more objects of interest according to an embodiment of the invention

At block 401 of the illustrated embodiment a multi-dimensional data set for the image volume is produced through pre-processing collected image data, such as by system unit 110. Various signal processing and/or image processing techniques may be utilized in providing an image volume data set according to embodiments of the invention, such as THI, demodulation, filtering, decimation, interpretation, amplitude detection, compression, frequency compounding, spatial compounding, black hole fill, speckle reduction, etc. An exemplary image volume represented by a multi-dimensional data set is shown in FIG. 5A as image volume 500. It should be appreciated that, although image volume 500 is shown as a cube, any multi-dimensional image volume may be utilized according to embodiments of the invention.

An advantages of acquiring a multi-dimensional data set, such as 3D ultrasound data, is that computer graphics framework may be used for placing virtual cameras in desired locations and orientations in the multi-dimensional space and subsequently creating lesser-dimensional (e.g., 2D) projected images of the acquired multi-dimensional data. These projected images represent a form of "compounded" information of the acquired data, and can be used to extract certain information from the data. More specifically, by identifying objects and/or other structures in these projected images and by using a plurality of virtual cameras in the multi-dimensional space a framework of computational geometry can be used to reconstruct a multi-dimensional representation of objects of interest from their lesser-dimensional projections.

Another role of projected images is that when the appropriate transfer and contrast enhancement functions are used they can provide a means for quickly showing the user whether the interventional instrument is contained within the multi-dimensional FOV. A maximum value operator used as a transfer function has been found to provide the best balance between computational complexity and quick visualization of an interventional instrument in projected images.

At block 402, various parameters are initialized for operation to identify one or more objects of interest in the multi-dimensional volume. For example, a number (N) of image projections (e.g., 2D image planes) or segments within the multi-dimensional data set is selected for use in identifying one or more objects of interest within the multi-dimensional data set. Although any number of image projections may be selected according to embodiments of the invention, preferred embodiments select two or more image projections. The larger the number of image projections selected, the greater the accuracy and/or certainty with respect to object identification and/or location. However, the larger the number of image projections selected, the greater the processing time/power utilized in identifying or locating the object of interest. Accordingly, such considerations are preferably considered in selecting a number of image projections for use with respect to any particular embodiment.

According to the illustrated embodiment, a loop counter (i) is initialized at block 402 for controlling operation of subsequent processing blocks. Specifically, the loop counter of the illustrated embodiment is set to the value 1 for controlling iterative processing with respect to blocks 403-408 described below.

At block 403, a virtual camera or "view" position and orientation is selected for a current image projection of the N image projections to be used (here, the first image projection because i=1). The foregoing virtual camera position may be any position determined to provide a useful view into or through at least a portion of the image volume. The virtual camera orientation, defining the resulting view orientation, may likewise be any orientation determined to provide a useful view into or through at least a portion of the image volume. For example, a virtual camera position may be selected to be the top center of image volume 500 (position 501), with a virtual camera orientation to provide a view straight down into the image volume (e.g., to produce image projection 510). Of course, depending upon the imaging technology used, the objects to be identified, the presence of various obstructions or other items in the image volume, etc., other virtual camera positions and/or orientations may be selected according to embodiments of the invention. Moreover, according to embodiments of the invention, the virtual camera position and/or orientation is altered from image projection to image projection of the N image projections in order to obtain segmented data with respect to the location of the object of interest. Accordingly, selection of virtual camera positions and orientations may be made to provide desired relationships between multiple image projections utilized according to embodiments of the invention (e.g., to provide desired relative spacing between image projections, to sufficiently cover one or more dimension of the image volume to sample and/or avoid particular areas or features within the image volume, etc.).

At block 404, an image projection for the selected virtual camera position and orientation is generated (e.g., image projection i). For example, in the foregoing example, image projection 510 is generated. It should be appreciated that an actual image need not be generated according to embodiments of the invention. For example, image plane data representing a particular view may be analyzed according to embodiments of the invention for interventional instrument identification without an image having been generated or displayed.

One or more putative location of one or more desired objects is identified within the image projection at block 405. For example, where the location of interventional apparatus 130 within image volume 500 is to be determined, a putative location (e.g., location 511) of that portion of interventional apparatus 130 appearing within image projection 510 may be identified.

The foregoing identification of interventional apparatus 130 may be performed automatically, semi-automatically, manually, or a combination thereof according to embodiments of the invention. For example, embodiments of the present invention may operate to semi-automatically identify interventional instruments by enabling a user to provide input, such as through operation of a pointing device, touch screen, input of coordinates, etc., to select location 511 as a putative location of interventional apparatus 130. Additionally or alternatively, automatic identification of interventional instruments may be provided with respect to subsequent frames of a moving image through tracking the user identified putative locations, or features thereof (e.g., putative locations may initially be identified through user input while subsequent putative locations may be identified without user input such as using techniques to track or otherwise identify features corresponding to the initial putative locations in subsequent frames of a moving image, to provide image plane updating in near real-time).

Semi-automatic operation provided according to embodiments of the present invention may be adapted to facilitate user selection of putative locations through the use of an image volume survey mode as shown and described in the above identified patent application entitled "Systems and Methods for Image Presentation for Medical Examination and Interventional Procedures." For example, selection of virtual camera position and orientation (block 403) and generation of image projections (block 404) may be provided by a survey mode wherein a user is enabled to survey the entire image volume by stepping through sequential image projections (image cross-sections). Such a survey facilitates a user easily identifying one or more best images for putative object location identification. Moreover, by restricting the degrees of freedom available to the user, understanding the relationship of objects represented in each such image projection from projection to projection and identifying such objects by a user is facilitated.

Embodiments of the invention preferably operate to automatically select location 511 as a putative location of interventional apparatus 130, such as using fuzzy logic and/or other machine implemented identification logic. Logic algorithms may operate to identify relative brightness, object shape, relative location, segment-to-segment relationships, tissue motion, elasticity, etc. in order to identify an object as a putative interventional instrument within a particular multi-dimensional volume segment. For example, interventional apparatus 130 is likely to be comprised of a different material (e.g., metal or plastic) than the surrounding material (e.g., living tissue) of image projection 510, thereby providing an identifiable attribute difference (e.g., relative brightness) which may be identified by machine logic. Similarly, interventional apparatus 130 is likely to have attributes (e.g. a regular or known shape) which facilitate machine logic identifying interventional apparatus 130 within image projection 510.

At block 406, a determination is made as to whether a putative location for interventional apparatus 130 has been identified in the current image projection (e.g., image projection 510). If no putative location for interventional apparatus 130 has been identified, processing according to the illustrated embodiment proceeds to block 412 wherein error trapping is performed. In the illustrated embodiment, such error trapping comprises concluding that interventional apparatus 130 cannot currently be tracked, informing the user of this conclusion, and providing a default image mode (e.g., operating in a traditional MPR image mode to provide a long axis or short axis MPR image). Of course, additional or alternative error trapping may be performed according to embodiments of the invention, such as to generate and analyze (blocks 403-405) one or more additional image projections before concluding that interventional apparatus 130 cannot be tracked, implementing one or more different/alternative putative location identification techniques (e.g., where automatic detection is used, soliciting user input to select a putative location, using different selection criteria, generating the image projection using a different image mode, etc.). Accordingly, failure to identify a putative location for interventional apparatus 130 may result in further processing in accordance with one or more of blocks 403-408 according to embodiments of the invention.

If a putative location for interventional apparatus 130 has been identified, processing according to the illustrated embodiment proceeds to block 406 wherein the loop counter (i) is incremented for controlling operation of subsequent processing blocks. Accordingly, at block 408 a determination is made as to whether the loop counter (i) is greater than the number (N) of image projections selected for use in identifying objects of interest within the multi-dimensional data set. If the loop counter is not greater than the number of image projections selected, all image projections have not been generated and analyzed and thus processing according to the illustrated embodiment returns to block 403. Accordingly, additional iterations of processing in accordance with blocks 403-408 may be performed to generate and analyze one or more additional image projections (e.g., image projections 520-550) and identify corresponding putative locations of interventional apparatus 130 (locations 521-551).

If, at block 408, the loop counter is greater than the number of image projections selected, all image projections have been generated and analyzed and thus processing according to the illustrated embodiment proceeds to block 409. At block 409 the putative interventional apparatus location information is utilized to calculate a position of interventional apparatus 130 within the multi-dimensional volume. Calculation of the interventional instrument position may implement segmentation principles as well as geometrical principles to identify the interventional instrument throughout the volume.

For example, embodiments using segmentation to extract a needle from 3D data sets can represent the needle by a parametric representation of a 3D curve. If it is assumed that the needle does not bend during insertion, then the needle can be represented by the parametric equation of a 3D line in space shown in the following equation:

$$\vec{P} = \vec{P}_O + \lambda \cdot \vec{u} \tag{1}$$

Where $\vec{P}_O$ represents the position vector of a point in the 3D line, $\vec{u}$ represents a unit vector defining the orientation of the 3D line, and $\lambda$ is any real number which corresponds to the various points with position vectors $\vec{P}$ in the 3D line. The assumption of the needle being a straight line while inserted into the human body may be more or less valid depending upon the type of needle used (e.g., gauge), and most times is valid in cases where targets are found in shallow depths (e.g., nerve blocks in upper extremities). In cases where needles are used to approach deeper structures (e.g., in cases of biopsies), the assumption of a needle being a straight line might break down. However, the assumption that a needle approximates a straight line continues to provide a first-order approximation of the needle shape, which depending on the particular clinical application may or may not be a satisfactory approximation.

In the case of clinical applications such as ultrasound-guided local anesthesia in upper extremities, an assumption that the needle approximates a straight line is realistic and accurate enough. Accordingly, embodiments of the invention operate under the assumption that interventional apparatus 130 comprises a linear device, and thus straight lines may be projected through one or more pairs of the putative interventional apparatus locations to calculate the location and orientation of interventional apparatus 130 within image volume 500.

Figure 5B:
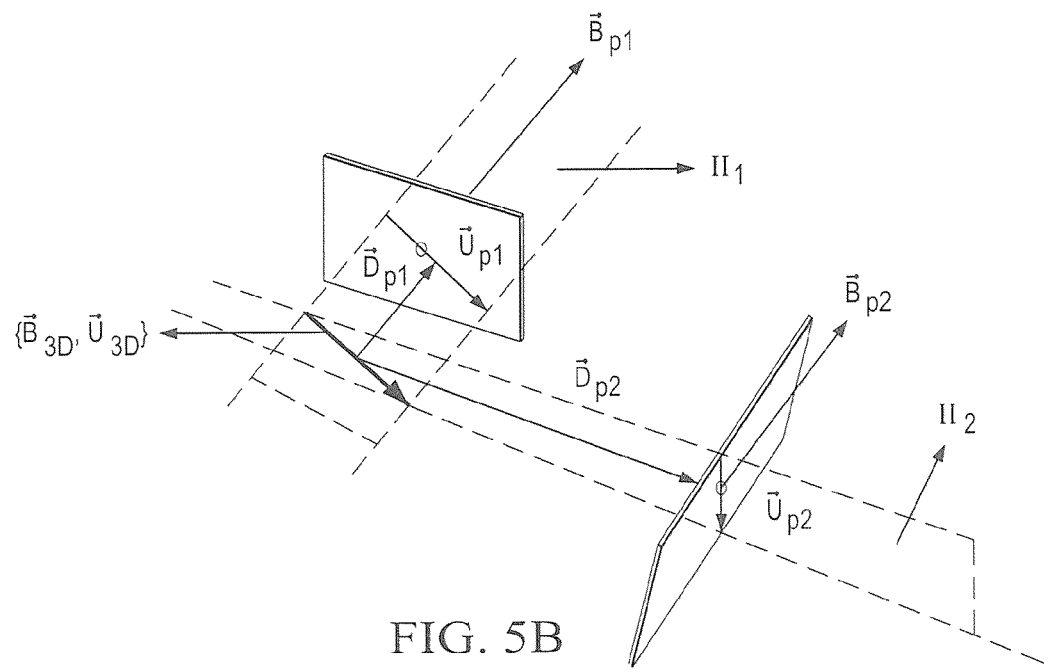

The reconstruction of a line in 3D space from projected images is a mathematical problem with a closed-form solution. Based on geometric principles at least 2 projected planes may be used to define a 3D line. This principle is shown graphically in FIG. 5B, where a 3D line (e.g., a needle) is projected into two planes, and then the problem of defining the 3D line reduces to defining the intersection between two planes $\Pi_1$ and $\Pi_2$. Each of the planes $\Pi_1$, $\Pi_2$ corresponding to a projected image is defined by the direction of projection and the 2D line identified in the projected image.

Figure 5C:
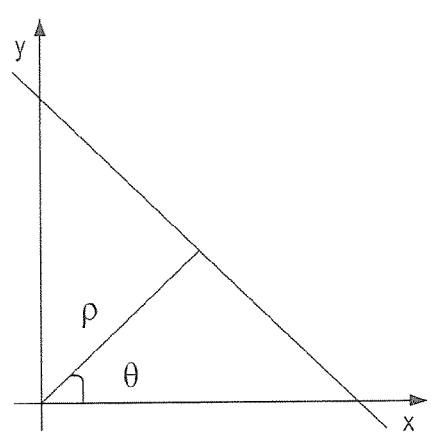

One of the most robust and reliable methods for detecting lines in 2D is the Hough transform. The Hough transform uses a polar coordinate to parameterize a 2D line, which avoids potential singularities and can properly represent a 2D line of any orientation. FIG. 5C shows the basic principle of the Hough transform.

Based on the polar coordinate system shown in FIG. 5C each line can be parameterized as:

$$\rho = x \cdot \cos\theta + y \cdot \sin\theta \tag{2}$$

It should be noted that each line in the x-y plane is represented by multiple pixels, whereas each line on the $\rho$-$\theta$ plane is represented by a single pixel.

Figure 6:
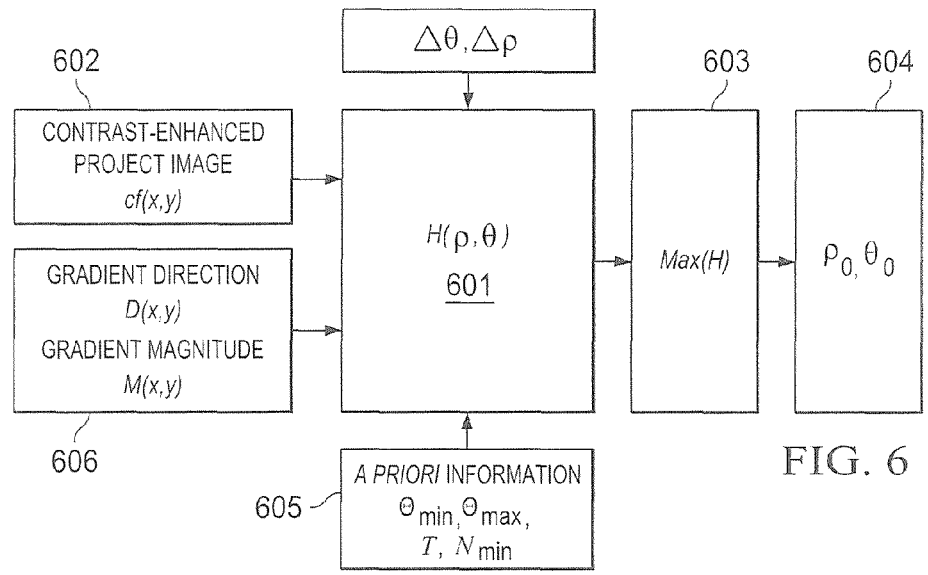
FIG. 6 shows a functional block diagram of logic providing line detection according to an embodiment of the invention.

FIG. 6 shows a functional block diagram of logic used to provide 2D line Hough-based detection algorithm 600 according to an embodiment of the invention. An image $H(\rho, \theta)$ (block 601 of FIG. 6) of a certain size, based on a given resolution for the $\rho$-$\theta$ plane, representing the line parameter space is constructed. All pixels of the image $H(\rho,\theta)$ are preferably initially set to an intensity of 0. To enhance the contrast of the projected interventional instrument, and preferably increase the success rate of the line detection algorithm, a contrast enhancement algorithm (block 602) may be used such that the original projected image f(x,y) is transformed to a contrasted enhanced image cf(x,y). An example of a contrast enhancement algorithm used according to embodiments of the invention is based on an S-curve parameterized by a rational exponential as shown in the following equation:

$$C(i) = \frac{1}{1 + e^{\alpha \cdot i - \beta}} \tag{3}$$

where $\alpha$ is a parameter controlling the slope of the exponential curve and $\beta$ is a parameter controlling the horizontal position of the curve, i is the input intensity value and C(i) is the output contrast enhanced value.

2D line Hough-based detection algorithm 600 of the illustrated embodiment traverses the pixels of the input image cf(x,y) and, for each (x,y) pixel that has an intensity value higher than T (block 605), increases the count of the corresponding ($\rho,\theta$) pixels (e.g., based on equation (2) above) by one (block 603). Once the entire image cf(x,y) has been traversed, the image $H(\rho,\theta)$ is traversed to identify the peak value (block 603). To eliminate noise in the peak detection algorithm, embodiments only consider accumulator bins (e.g., pixels of image $H(\rho,\theta)$) that exceed a certain value Nmin. This eliminates detections of lines by a few isolated pixels which accidentally happen to fall on the same line. A priori information, in addition to the aforementioned parameters, may be used (block 605), such as for restricting the possible interventional instrument projection angles to an interval [$\Theta$min, $\Theta$max]. This interval may be determined by the specific virtual camera location and the physical spatial relation between an imaging tool (e.g., transducer) and interventional instrument (e.g., needle).

Once the $H(\rho,\theta)$ plane has been formed, an interventional instrument projection line can be assigned the parameters $(\rho0,\theta0)$ (block 604) for which the following conditions are satisfied:

$$\begin{cases} \theta_0 \in [\Theta_{min}, \Theta_{max}] \\ H(\rho_0, \theta_0) = \text{Max}(H(\rho, \theta)) \\ H(\rho_0, \theta_0) > N_{min} \end{cases} \quad (4)$$

If none of the pixels in the $H(\rho,\theta)$ image satisfies the previous conditions, then it may be concluded that line detection has failed. From equation (4) it can be seen that the shape detection problem (in this case the shape of interest is a line) becomes a peak detection problem when using the Hough transform.

In order to reduce the probability of considering isolated points of high-intensity value as interventional instrument points, embodiments of 2D line Hough-based detection algorithm 600 form an image representing the gradient direction and magnitude of the pixels found in the projected image $f(x,y)$ (block 606). An efficient method for creating gradient direction and gradient magnitude images of a specific image is by using the first horizontal and vertical derivatives of a Gaussian kernel. Initially the image may be convolved by the two kernels and the two resulting images are preferably used with square root and arctan computations for form the gradient magnitude and gradient direction images respectively.

A very appealing property of the Hough transform is that it can accommodate for line discontinuities as long as there is sufficient signal in a substantial part of the interventional instrument. This may be a very important property according to some embodiments because some parts of an interventional instrument are often not visible in image data due the angle of incidence between the imaging illumination and the interventional instrument.

When using the Hough transform to detect lines it may be desirable to preprocess the image such that only true line candidate pixels are left in the image. It should be appreciated that in ultrasound images this is not a trivial task due to the speckle, which is due the constructive and destructive interference of ultrasound waives. However, the foregoing approach of using the projected images exhibits a great advantage over approaches that directly use the 2D ultrasound cross-sections. For example, a volume rendering operator, such as a line integral in 3D space simulating the phenomenon of light absorption as light travels through matter, acts as a spatial compounding operator, which increases the signal-to-noise ratio (SNR) by the effect of signal averaging. Therefore, in the projected image speckle is cancelled out and attenuated, whereas structures are enhanced. Furthermore, specialized transfer functions may be used to further enhance the structure of interest (e.g., interventional instrument). For example, transfer functions such as transfer functions based on various classification principles (e.g., the k-means algorithm), maximum intensity operator, etc. may be used to provide enhancement of structure of interest.

A potentially more computationally efficient approach of the Hough transform can be provided by the Radon transform. These two transforms can be proven to be different implementation approaches of the same operator where essentially the inner product of a shape with an image data set is computed. In addition, it can be proven that both of these transforms can be formulated as a template matching problem.

Using the notation presented above the Radon transform can be written as:

$$R(\rho, \theta) = \iint_{\mathfrak{R}^2} f(x, y)\delta(x\cos\theta + y\sin\theta - \rho)dxdy \quad (5)$$

The Radon transform can be computationally more efficient when the parameter space is constrained whereas for sparse data the Hough transform might be more efficient. In many cases, the Hough transform is sufficiently fast to provide near real-time computations. However, the Radon transform may be used where computational speed needs to be increased.

More than two projections may be utilized in identifying a interventional instrument according to embodiments of the invention, such as to address noise issues, to provide a technique that signals false positive interventional instrument identification, etc. For example, if 3 projections are chosen then 3 plane intersections will be defined, in which the ideal case will result in the same 3D line representing the interventional instrument. However, if these 3 lines are not (in a least square sense) significantly similar it can be concluded that different features in each projected plane are being detected.

By selecting appropriate putative interventional apparatus locations, multiple location and orientation results may be determined (e.g., a first line projected through the first pair of locations and a second line projected through the second pair of locations). For example, various combinations of locations 511-551 shown in FIG. 5A may be utilized in identifying an interventional instrument according to embodiments of the invention. Locations 531 and 541 may be utilized as a first pair of locations and locations 521 and 551 as a second pair of locations to identify 2 lines which will either result in the same 3D line representing the interventional instrument of 2 lines which are not significantly similar, thus suggesting that different features are being detected in each projected plane.

Embodiments of the invention operate to determine $$k = \binom{N}{2}$$

lines defined by the foregoing putative interventional instrument locations. Such results may be compared to determine if the location and orientation of interventional apparatus 130 has been made to a desired degree of accuracy. For example, if the number of lines is greater than one (e.g., k>1), then some amount of discrepancy exists between the calculated results from various pairs of putative interventional apparatus locations. Accordingly, multiple sets of putative interventional instrument locations are cross-checked in order to confirm that each such set identifies a same interventional instrument location, or identifies interventional instrument locations within a threshold level of accuracy, according to embodiments of the invention. Additionally or alternatively, different putative interventional instrument location identification techniques, such as user selected, relative brightness, object shape, etc., may be utilized to cross-check or otherwise confirm accuracy of interventional instrument identification according to embodiments of the invention.

At block 410 of the illustrated embodiment, if more than one object location and orientation is determined an error metric (e) and object parameters are determined. For example, a least square method may be used to compute an error metric for determining if the calculated interventional apparatus locations and orientations are sufficiently consistent to result in desired operation.

At block 411, a determination is made as to whether the error metric (e) is greater than an acceptable error threshold (T). If the error metric is greater than the acceptable error threshold, then the calculated interventional apparatus locations and orientations are determined not to be sufficiently consistent to result in desired operation and thus processing according to the illustrated embodiment proceeds to block 412 for error trapping as discussed above. However, if the error metric is greater than the acceptable error threshold, then the calculated interventional apparatus locations and orientations are determined to be sufficiently consistent to result in desired operation and thus processing according to the illustrated embodiment proceeds to block 413 for generation of an appropriate image for showing interventional apparatus 130.

Once projections of the 3D interventional instrument are detected in projected images, embodiments operate to determine the equation that describes the interventional instrument in 3D. Continuing with the foregoing example of an interventional instrument having a straight line geometry, it can be seen in FIG. 5B that the desired line is defined by the intersection of planes $\Pi_1$ and $\Pi_2$. Each of these planes is defined by the direction of projection used to create the corresponding projected image, vectors $\vec{D}_{p1}$ and $\vec{D}_{p2}$ in FIG. 5B, the vector of the line detected in the 2D projected image, vectors $\vec{U}_{p1}$ and $\vec{U}_{p2}$ in FIG. 5B. Furthermore, in addition to two vectors one point is required to fully determine each of the planes $\Pi_1$ and $\Pi_2$, points $\vec{B}_{p1}$ and $\vec{B}_{p2}$ in FIG. 5B.

The parametric equations of planes $\Pi_1$ and $\Pi_2$ are given by the equations:

$$\left\{ \begin{array}{l} \Pi_1 : \vec{n}_1 \cdot \vec{P} + d_1 = 0 \\ \Pi_2 : \vec{n}_2 \cdot \vec{P} + d_2 = 0 \end{array} \right\} \quad (6)$$

Where $\vec{P}$ represents the position vector of a point belonging to the plane of interest, $\vec{n}_1$ and $\vec{n}_2$ represent the normal unit vectors to the planes $\Pi_1$ and $\Pi_2$ correspondingly $d_1$ and $d_2$ are constants associated with the planes $\Pi_1$ and $\Pi_2$ correspondingly (indicating the distance of the origin of the coordinate system from planes $\Pi_1$ and $\Pi_2$ correspondingly). The normal vector and constants can be computed by the following equations:

$$\left\{ \begin{array}{l} \vec{n}_1 = \vec{U}_{P1} \times \vec{D}_{P1}, \text{ and } d_1 = -\vec{n}_1 \cdot \vec{B}_{P1} \\ \vec{n}_2 = \vec{U}_{P2} \times \vec{D}_{P2}, \text{ and } d_2 = -\vec{n}_2 \cdot \vec{B}_{P2} \end{array} \right\} \quad (7)$$

Based on these two planes $\Pi_1$ and $\Pi_2$ it can be shown that the 3D line representing the interventional instrument in 3D space shown in equation (1) is given by:

$$\vec{P} = \frac{\left( \left| \begin{array}{cc} n_{1y} & n_{2y} \\ d_1 & d_2 \end{array} \right|, \left| \begin{array}{cc} d_1 & d_2 \\ n_{1x} & n_{1x} \end{array} \right|, 0 \right)}{\left| \begin{array}{cc} n_{x1} & n_{x2} \\ n_{y1} & n_{y2} \end{array} \right|} + \lambda \cdot (\vec{n}_1 \times \vec{n}_2) \quad (8)$$

Using equation (8) to define the position and orientation of the 3D line representing the interventional instrument planes may be extracted from the 3D data set that contain the interventional instrument.

Figure 7:
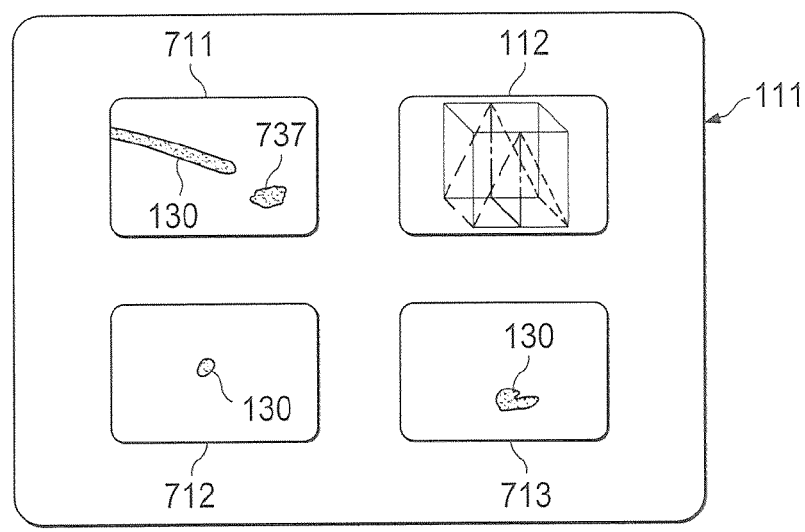
FIG. 7 shows an exemplary image as may be generated to include various sub-images by the system of FIG. 1A.

Using the interventional apparatus location and orientation information derived above, embodiments of the invention identify one or more appropriate image plane for displaying interventional apparatus 130. For example, an image plane which has an axis corresponding to a longitudinal axis of interventional apparatus 130 and which includes interventional apparatus 130 (and perhaps another object, such as target anatomy), may be selected (e.g. as an A-plane for a multi-image presentation) for generating a desired image. Sub-image 711, shown in image 111 of FIG. 7, provides display of interventional apparatus 130 and target 730 using an image plane which has an axis corresponding to a longitudinal axis of interventional apparatus 130.

According to embodiments of the invention, one or more MPR images are generated to show interventional apparatus 130 using the foregoing interventional apparatus location and orientation information. For example, multiple orthogonal planes that contain interventional apparatus 130 may be selected and the corresponding images displayed. Image 111 of the illustrated embodiment of FIG. 7 includes sub-image 712 (e.g., a B-plane showing a vertical cross-sectional plane orthogonal to the A-plane view) and sub-image 713 (e.g., a C-plane view showing a horizontal cross-sectional plane orthogonal to the A-plane view) in addition to sub-image 711 wherein their image planes are orthogonal to one another and to that of sub-image 711.

Having identified interventional apparatus 130 within a multi-dimensional volume, embodiments of the invention operate to cause an image or images for appropriately displaying the object or objects to be generated and displayed, wherein the objects' movement within the volume is shown in near real-time. It should be appreciated that not only may the image within a particular image plane be updated in near real-time, but the orientation of the particular image plane used may updated in near real-time (e.g., using the steps set forth above) to continuously display the desired information. Accordingly, image planes may be dynamically adjusted to display an interventional apparatus and/or other objects throughout an interventional procedure or other activity.

Additional or alternative images to those mentioned above may be displayed, such as to provide a view of target 737, to provide the aforementioned pictogram showing a relative orientation of a corresponding sub-image, etc., if desired. One or more reference indicator in the form of a marker or markers to correlate sides, dimensions, etc. of an image volume dataset with the physical world may be provided in, on, or in association with the foregoing generated image showing interventional apparatus 130 according to embodiments of the invention. According to embodiments of the invention, the image marker comprises a representational pictogram (e.g., pictogram 112 of FIGS. 1 and 7) providing orientation, spatial, and/or relational information with respect to the generated image. The details with respect to the generation and use of such an image marker are provided in the above referenced patent application entitled "Systems and Methods for Image Presentation for Medical Examination and Interventional Procedures."

Figure 8A:
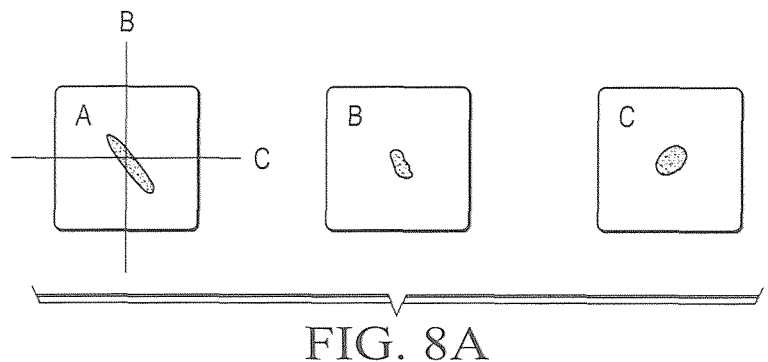
FIG. 8A shows conventional orthogonal MPR image frames.
Figure 8B:
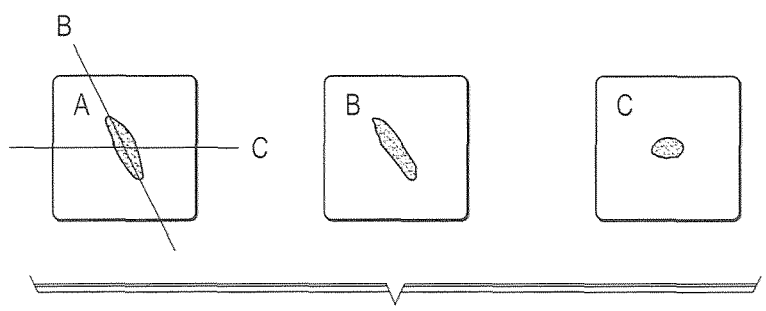
FIG. 8B shows non-orthogonal MPR image frames according to an embodiment of the present invention.

It should be appreciated that the foregoing image planes for appropriately displaying the object or objects are not constrained to conventional orthogonal MPRs, and thus may include non-orthogonal MPRs. Directing attention to FIG. 8A, conventional orthogonal MPR image frames are shown as image frames A, B, and C, wherein each image frame is orthogonal to the other image frames. Such orthogonal image frames may or may not align with an object of interest, and thus may not provide an optimum view of the object of interest. FIG. 8B shows non-orthogonal MPR image frames, such as may provide images of FIG. 7, in accordance with embodiments of the invention. In the embodiment illustrated in FIG. 8B, image planes A and B are orthogonal with respect to each other and image planes A and C are orthogonal with respect to each other, however image planes B and C are non-orthogonal with respect to each other. Image plane B is preferably selected as described above to provide a desired view of an identified object of interest, and thus is oriented accordingly. Image plane C preferably corresponds to a given depth in the real world subject.

Figure 8C:
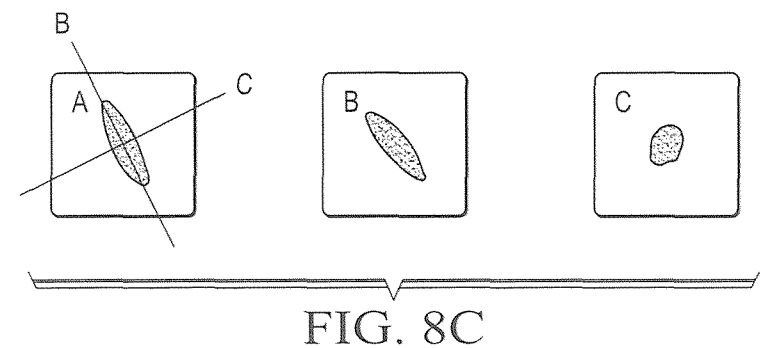
FIG. 8C shows orthogonal MPR image frames where an image plane is selected to provide a desired view of an identified object of interest according to an embodiment of the invention.

It should be appreciated that orthogonality may be provided with respect to each such image plane when an image plane for appropriately displaying the object or objects is selected as described herein. Directing attention to FIG. 8C, orthogonal MPR image frames are shown where image plane B is selected as described above to provide a desired view of an identified object of interest, and thus is oriented accordingly. However, embodiments of the invention implement non-orthogonal MPR image frames, such as shown in FIG. 8B, so as to provide constant orientation of various image frames (e.g., implementing a constant image coordinate system) for ready interpretation of the images by a user.

Foregoing embodiments provide a workflow useful, for example, with respect to ultrasound-guided local anesthesia which reduces the complexity of the procedure using state-of-the-art multi-dimensional ultrasound imaging. The workflow and the procedure is greatly simplified according to embodiments because there is a higher probability that an interventional instrument, such as a needle, will be contained within a 3D volume rather than a thin slab 2D image, wherein operation of embodiments identifies the interventional instrument within the 3D volume and properly displays it within the 2d image. An anesthesiologist, for example, will typically still need to manipulate a tool, such as an ultrasonic transducer, to find the anatomy of interest, but after that point there will be much less or no manipulations of the tool while manipulating the interventional instrument. For example, during needle insertion a system of an embodiment will continuously track the needle and present one or more 2D planes containing the needle to the physician. Moreover, display of additional 2D planes (compared to the single plane available in 2D ultrasound) presented to the clinician should enhance the understanding of the anatomy with respect to the interventional instrument and increase the confidence in performing the procedure.

It should be appreciated that, although embodiments of the invention have been described above with reference to a linear configuration of objects of interest, the concepts of the present invention are not limited to use with respect to any particular geometry of object. For example, a curved interventional instrument may be identified using the flow diagram of FIG. 4 discussed above through use of curve fitting techniques in association with the aforementioned pairs of putative interventional apparatus locations. Moreover, although perhaps requiring additional computational power, embodiments of the invention may utilized additional parameters to identify objects having complex and/or changeable geometries. For example, a flexible object, such as a catheter, may be identified using flexibility information (e.g., maximum/minimum curve radii) and curve fitting techniques.

Although embodiments have been described herein with reference to identifying one object of interest, the concepts of the present invention may be utilized in identifying any number of objects of interest in an image volume. Such objects may be of different material compositions including but not limited to metal alloys, plastics, or composites, they may further be different shapes and sizes including but not limited to linear, circular, semi-linear, or die-cast, and they may further have different rates of movement within any combination of the axial dimensions of the subsurface volume.

Although embodiments have been described herein with respect to use of system 100 for interventional procedures, it should be appreciated that systems adapted according to the concepts of the present invention may be for any number of uses. For example, embodiments of the present invention may be utilized for identifying tools, such as hydrocarbon drilling apparatus, disposed beneath the Earth's surface.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of operating an ultrasound imaging device to determine location and orientation information for an interventional device, comprising:
    obtaining a multi-dimensional data set of a subject that includes at least a portion of an interventional device, wherein the multi-dimensional data set is generated by the ultrasound imaging device;
    determining location and orientation information for said interventional device in said multi-dimensional data set by:
        defining two or more two-dimensional projected planes with projection vectors having different orientations;
        projecting the multi-dimensional data set onto the two or more two-dimensional projected planes to detect lines in each of the two or more two-dimensional projected planes that represent a projection of the interventional instrument onto the two-dimensional projected planes; and
        determining location and orientation information for said interventional device based on the detected lines in each of the two or more two-dimensional projected planes.

2. The method of claim 1, wherein said multi-dimensional data set represents a volume having at least 3 spatial dimensions.

3. The method of claim 1, further comprising:
    selecting a virtual camera position and orientation for each of the two or more two-dimensional projected planes; and
    generating an image projection for each of the virtual camera positions and orientations.

4. The method of claim 3, wherein detecting a line further comprises:

receiving an indication from a user of an object within a selected two-dimensional projected plane as representing a location of said interventional device within said selected two-dimensional projected plane.

5. The method of claim 4, wherein said determining location and orientation information for said interventional device comprises:
selecting at least one pair of detected locations for the interventional device; and
projecting an interventional device geometry through said pair of detected locations in one or more of the two-dimensional projected planes.

6. The method of claim 4, wherein said determining location and orientation information for said interventional device comprises:
selecting at least two pairs of detected device locations; and
projecting an interventional device geometry through each said pair of detected locations in one or more of the two-dimensional projected planes.

7. The method of claim 6, further comprising:
determining if said location and orientation information provide a reliable indication of a location and orientation of said interventional device.

8. The method of claim 7, wherein said determining if said location and orientation information provide a reliable indication of said location and orientation of said interventional device comprises:
determining an error metric with respect to said location and orientation information; and
comparing said error metric to an error threshold.

9. The method of claim 3, wherein detecting a line further comprises:
selecting by operation of a logic algorithm an object within a selected two-dimensional projected plane as representing a location of said interventional device within said selected two-dimensional projected plane.

10. The method of claim 9, wherein said selecting an object comprises:
identifying said object as a function of a relative attribute.

11. The method of claim 9, wherein said selecting an object comprises:
identifying said object as a function of a known attribute of said object.

12. The method in claim 1, further comprising:
displaying movement of said interventional device in near real-time in said image.

13. The method in claim 1, further comprising:
locking an orientation of said displayed image to said one or more image planes.

14. The method of claim 1, further comprising:
displaying a pictogram representing an orientation of said one or more image planes in said multidimensional data set.

15. The method of claim 1, further comprising:
displaying one or more image planes of images generated from said multi-dimensional volume, wherein at least one image plane is non-orthogonal to at least one plane of said two or more two-dimensional projected planes.

* * * * *